(12) United States Patent  
Cuellar

(10) Patent No.: US 11,538,579 B2  
(45) Date of Patent: Dec. 27, 2022

(54) MEDICAL MANAGEMENT SYSTEM

(71) Applicant: Alberto D. Cuellar, The Woodlands, TX (US)

(72) Inventor: Alberto D. Cuellar, The Woodlands, татTX (US)

(*) Notice: Subject to any disclaimer, the term of this patent is extended or adjusted under 35 U.S.C. 154(b) by 863 days.

(21) Appl. No.: 15/191,879

(22) Filed: Jun. 24, 2016

(65) Prior Publication Data

US 2017/0372022 A1    Dec. 28, 2017

(51) Int. Cl.

| | |
|---|---|
| *G16H 40/20* | (2018.01) |
| *G06F 21/62* | (2013.01) |
| *G06Q 10/10* | (2012.01) |
| *G06Q 40/08* | (2012.01) |

(52) U.S. Cl.  
CPC ......... *G16H 40/20* (2018.01); *G06F 21/6245* (2013.01); *G06Q 10/10* (2013.01); *G06Q 40/08* (2013.01)

(58) Field of Classification Search  
CPC ..... G16H 40/20; G06F 21/6245; G06F 19/00; G06Q 10/10; G06Q 40/08  
See application file for complete search history.

(56) References Cited

U.S. PATENT DOCUMENTS

| | | | | |
|---|---|---|---|---|
| 8,027,849 | B2* | 9/2011 | Johnson | G06Q 10/06 705/2 |
| 2007/0185733 | A1* | 8/2007 | Roady | G06Q 10/10 705/2 |
| 2011/0125539 | A1* | 5/2011 | Bollapragada | G06Q 10/0631 705/7.12 |
| 2013/0339969 | A1* | 12/2013 | Koski | G06Q 10/10 718/103 |

* cited by examiner

*Primary Examiner* — Eliza A Lam  
(74) *Attorney, Agent, or Firm* — Nolte Lackenbach Siegel

(57) ABSTRACT

A method of managing medical data, the method including defining at least one participating object and defining an operational relationship between the at least one participating object and a second participating object. The method also includes defining an event capability for the participating object, defining an event role for the at least one participating object, and defining a financial profile for the at least one participating object. The method may further include selecting at least one participating object, generating an event for the at least one selected participating object, and delivering data representative of the generated event to a user.

20 Claims, 10 Drawing Sheets

FIG. 7

MEDICAL MANAGEMENT SYSTEM

BACKGROUND OF THE INVENTION

Healthcare has become expensive and difficult to deliver for a variety of reasons. One reason healthcare has become expensive and difficult to deliver is because of the complexities inherent in medical science, which are compounded by various complex and chaotic mechanisms required for appropriate execution of providing services and products. Services and products may include the provision of medical services, such as medical professional appointments, hospital visits, surgeries, and the like, as well as the requisition of products, including products used in medical treatment and maintenance care.

The complexity of medical systems has developed over time, with medical systems becoming more complex as medicine and treatment options have developed. The complexity has further developed as a result of regulatory and economic pressures from the government and insurance companies. Monetary expansion in the medical industry in the form of government programs and insurance companies has further produced a culture of inefficient clinical and business processes that has, over time, resulted in limiting the medical industry's ability to deliver medical services and products. At the same time that governmental programs and insurance companies have become more pervasive in medical systems, escalating consumer costs, caused by operational inefficiencies have hampered a patient's ability to obtain necessary access to medical care.

While the medical industry has attempted to remove operational inefficiencies through computerization, the existing solutions have not addressed fundamental details of clinical and business processes that are at the core of the inefficiencies. Paradoxically, the solutions the medical industry has attempted to implement in order to solve the operational inefficiencies has increased cost and created even more obstructions to medical service delivery.

BRIEF SUMMARY OF THE INVENTION

According to one aspect of one or more embodiments of the present invention, a method of managing medical data, the method including defining at least one participating object and defining an operational relationship between the at least one participating object and a second participating object. The method also includes defining an event capability for the participating object, defining an event role for the at least one participating object, and defining a financial profile for the at least one participating object. The method may further include selecting at least one participating object, generating an event for the at least one selected participating object, and delivering data representative of the generated event to a user.

According to one aspect of one or more embodiments of the present invention, a computer system according to embodiments of the present invention may include a processor, a system memory device, a network interface device, and a storage device. The storage device may include a non-transitory computer readable medium including software instruction that, when executed by the processor perform various operations. The various operations may include defining at least one participating object, defining an operational relationship between the at least one participating object and a second participating object. The operation may further include defining an event capability for the participating object, defining an event role for the at least one participating object, and defining a financial profile for the at least one participating object. After the parameters are defined, the operation may include selecting at least one participating object, generating an event for the at least one selected participating object, and delivering data representative of the generated event to a user.

According to one aspect of one or more embodiments of the present invention, a method of managing medical data, the method including defining at least one participating object, an operational relationship between the at least one participating object and a second participating object, an event capability for the participating object, and event role for the at least one participating object, and a financial profile for the at least one participating object. The method further including modifying at least one of the event capability for the participating object, and deliver data representative of the modification to at least one of the at least one participation object and the second participating object.

Other aspects of the present invention will be apparent from the following description and claims.

BRIEF DESCRIPTION OF THE DRAWINGS

FIG. 7 is a data entry form according to embodiments of the present invention.

DETAILED DESCRIPTION OF THE INVENTION

Figure 1:
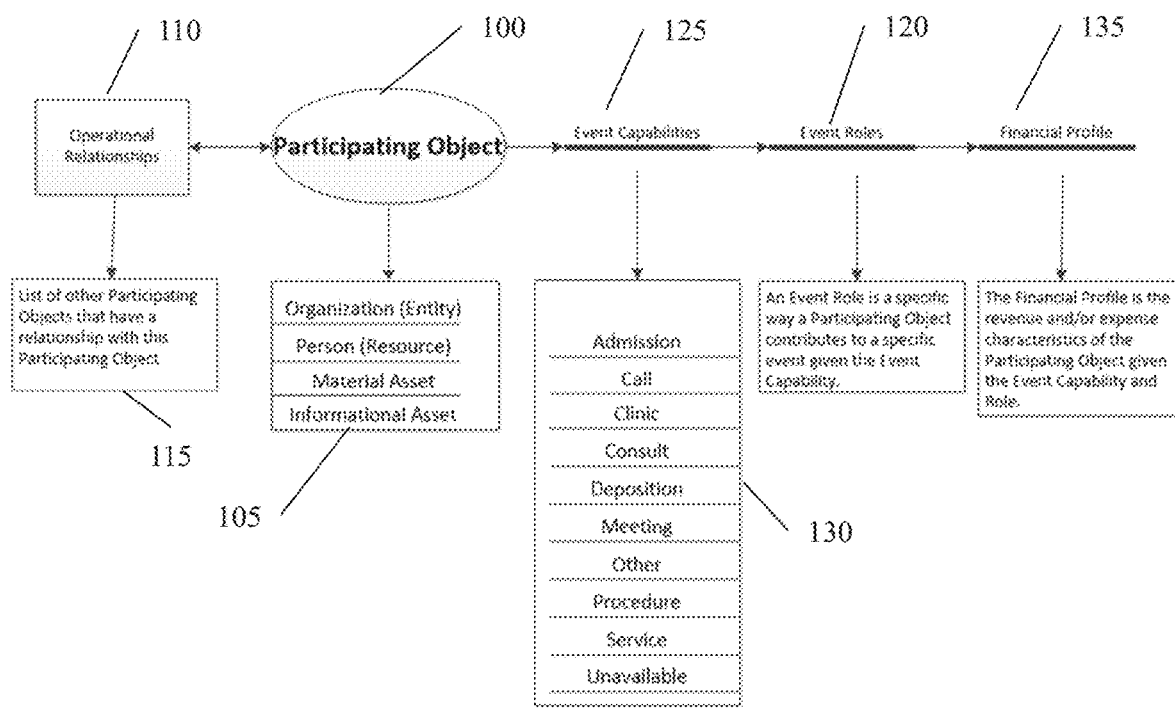
FIG. 1 is a flowchart diagram illustrating a method of managing medical data according to embodiments of the present invention.

One or more embodiments of the present invention are described in detail with reference to the accompanying figures. For consistency, like elements in the various figures are denoted by like reference numerals. In the following detailed description of the present invention, specific details are set forth in order to provide a thorough understanding of the present invention. In other instances, well-known features to one of ordinary skill in the art are not described to avoid obscuring the description of the present invention.

The healthcare industry has grown exponentially in both size and complexity over the past several decades. As a result of changes in insurance, government regulations, treatment protocols, and technological advancements many different entities interact on a daily basis in the provision of services to patients or clients. Various different entities must interface in order to coordinate patient care. Examples of interfacing entities include, for example, medical providers, patients, hospitals, medical facilities, suppliers, service providers, and patients.

As used in current medical service operations the different healthcare entities, resources, and assets act largely independently, thereby causing duplication of work, as well as repetitive labor intensive work tasks. For example, information may be distributed individually to each healthcare entity, resource, or asset, as well as certain third parties that may be working with the entity, resource, or asset. Thus, a single change in a medical service operation may result in the manual and repetitive task of updating each of the parties involved in the operation. This inefficiency is further exacerbated by the common occurrence of multiple changes occurring during the pendency of a medical service operation. For example, in the scheduling of one medical service operation, multiple entities, resources, and assets may have schedules that depend on one another. In one example, a date change may occur that changes an entities schedule, which may thereby cause changes to the schedules of other entities, resources, and/or assets.

In current systems, each additional entity, resource, and/or asset would be notified of the change to the first entity, which would thereafter modify their respective dates accordingly. However, the date change may not be workable for one of the additional entities, resources, and/or assets, which would then cause a second layer of duplicative work, as the additional entities, resources, and/or assets are required to communicate separately in order to determine a solution. In the present invention, different healthcare entities, resources, and assets are tied together using a data structure that allows for the centralized and real-time communication between the entities, resources, and assets. Because the entities, resources, and assets are fundamentally linked, a single change to one of the components can be resolved without the need for duplicative work tasks in order to determine and/or achieve a solution.

All medical information and data exchange systems must comply with current regulations promulgated under The Health Insurance Portability and Accountability Act of 1996 ("HIPAA"), which refers to an Act to amend the Internal Revenue Code of 1986 to improve portability and continuity of health insurance coverage in the group and individual markets, as well as to improve health insurance coverage in group and individual markets. The amendment was also promulgated to combat waste, fraud, and abuse in health insurance care and delivery and to improve access to long-term care services and coverage to simplify the administration of health insurance. One of the side-effects of HIPAA relates to the HIPAA privacy rules, which regulate the use and disclosure of protected health information that is held by covered entities, such as health care clearinghouses, employer sponsored health plans, health insurers, and medical service providers. Protected health information generally refers to any part of an individual's medical record or payment history. Medical management systems, such as those disclosed herein, must meet all relevant HIPAA standards with respect to protected health information and/or any information that is covered by HIPAA privacy rules.

Embodiments of the present invention may provide a centralized medical management system for managing medical data, monitoring medical events, and providing information for participants in medical events. The centralized system may thus define specific functions for each participant in the event, inform other participants in the event as to the status of other participants, and allow the centralized distribution of data. By centralizing the dissemination of data, each party to the medical event will be able to better plan for an event, which may ultimately increase efficiency, decrease patient costs, and provide for a more organized and functional event that increase patient care.

Referring to FIG. 1, a flowchart diagram illustrating a method of managing medical data according to embodiments of the present invention is shown. In this embodiment, managing medical data starts with defining a participating object 100. A participating object may include, for example, an organization, an entity, a person, a resource, a material asset, or an informational asset (illustrated in box 105). The participating object 100 defines a principal starting point from which other aspects of the medical management of data may derive.

In one embodiment, an organization, or entity, may include for example a medical practice group, a hospital, a clinic, a medical supplier, etc. The organization or entity is a participating object that provides a predefined role in the administration of medical services. For example, if the object is a hospital, a clinic, or a medical practice, the role of the object may be to supply resources and assets for procedure events or otherwise to provide resources to perform a certain medical procedure. In the event the participating object is a medical supplier, the role may be to supply products and services for a particular procedure. Similarly, if the participating object is a particular medical practice group, such as an anesthesia group, the role of the object may be to provide a particular service for a patient. For example, in the case of an anesthesia group, the role of the object would be to provide anesthesia services for a patient during a procedure. Those of ordinary skill in the art will appreciate that the examples provided above are not limiting on the scope of the present application. In defining a role for an organizational or entity participating object, various other types of organizations and entities may be included that provide roles during medical procedures.

The participating object 100 may further include a person or a resource. When the participating object 100 is a person or a resource, the participating object 100 may provide a defined role during the administration of medical services. Examples of objects as people or resources include, for example, a nurse, a medical technician, a surgeon, a physician assistant, a representative, etc. The role of the person or resource may be predefined and particular to a given procedure or provide a different role within the administration of medical services. For example, if the object is a nurse, the defined role could be to provide services as a circulator, while if the object is a technician, the role could be to provide surgical technician services during administration of a medical service. Similarly, if the object is a surgeon, the role may be to perform a particular procedure, while the role of a physician assistant may be to assist the surgeon during the procedure. In still other embodiments, the object may be a representative, whose role may be to provide management, such as, for example, technical product management. Those of ordinary skill in the art will appreciate that various participating objects 100 may be present during the administration of medical services and each participating object that is a person or resource may have a predefined role within a certain medical procedure.

The participating object 100 may also be a material asset. Examples of material assets may include physical assets that are used during medical procedures. For example, a material asset may include a surgical facility that provides the role of making available operating rooms, suites, and other equipment. A material asset may also be a certain piece of equipment that is used during medical procedures such as, for example, an image intensifier that provides the role of supplying inter-op images. Material asset objects may also include surgical implants or other equipment that is used during a procedure, which provides a predefined role during the procedure. Those of ordinary skill in the art will appreciate that there is a wide range of material assets that may be used in the provision of medical services. As such, the specific material assets described above should not limit the scope of the present invention.

The participating object 100 may also include an informational asset. Informational assets may include any type of data that may be stored, delivered, modified, or otherwise used or provided by a computer. Examples of informational assets include documents, lists, images, demographics, spreadsheets, etc. In a medical procedure, various types of informational assets may be used by participating objects in order to complete the event. Informational assets may provide the role of supplying specialized information during medical procedures. For example, an informational asset may be a specialized person within a practice group that has a predefined role that includes the provision of information for another object during a medical procedure. In a medical procedure involving anesthesia, an informational asset may be an anesthesia technician that provides a role of setting up anesthesia equipment and supplies. During the same medical procedure, a second informational asset may be a certified registered nurse anesthesiologist, which provides the informational services of managing a patient under anesthesia. Informational assets may provide various services that, in additional to providing information during or about a medical procedure, may also directly participate in a medical procedure.

Participating objects 100 provide a starting point through which other data about a medical procedure may be defined. After the participating objects 100 are defined, operational relationships 110 between the various participating objects 100 may be defined. In order to define operational relationships 110, a list of other participating objects that have a relationship with participating object 100 is formed (illustrated in box 115). The operational relationships 110 may include how the participating objects 100 interact, how one participating object 100 uses another participating object 100, how the participating objects 100 are related, etc. For example, a first participating object 100 may be a hospital, and another participating object 100 may be a nurse. The operational relationship 110 may include data that indicates that the nurse works or available to work at the hospital. The hospital may also have a relationship with another participating object 100, a surgical facility within or otherwise available to the hospital. Further, the hospital may have an operational relationship 110 with a medical device supplier. Those of ordinary skill in the art will appreciate that many various participating objects 100 may have defined operational relationships 110 with any number of other participating objects 100.

Operational relationships 110 may also include security parameters and permissions that define the hierarchy of access to information. For example, operational relationships 110 may allow different participating objects 100 access to different information related to an event. During a medical procedure involving a physician and a third party supply company, operational relationships 110 may be defined giving the physician access to patient information that a third party supply company does not need or is legally not allowed to access. Thus, operational relationships 110 may be defined so that a need-to-know hierarchy is created, thereby giving certain participating objects 100 greater access to information within the system.

Defining the operational relationships 110 further allows for the selection of appropriate participating objects 100 for a particular procedure. For example, because the operational relationships 110 are defined for each participating object, when determining which participating objects 100 are used in a particular procedure, a coordinator putting together the procedure has advance knowledge of all possible participating objects 100. Thus, rather than make multiple calls to determine availability of a particular participating object 100 for a procedure, the administrator will know the pool of participating objects 100 from which a particular participating object 100 may be selected.

Each participating object 100 may also have specific event roles 120 that define the way the participating object contributes to a specific event given a particular event capability 125. Event capabilities refer to specific types of events that may occur and whether the participating object can participate in the particular event. Depending on the type of participating object 100, the event capabilities 125 may vary widely. For example, a participating object 100 that is a person or a resource may be able to provide a consultation, while a material asset, such as a medical device would not be able to provide a consultation. However, both a person and a material asset may have event capability 125 for a particular procedure.

Examples of common event capabilities 125 include admissions, calls, clinic, consultations, depositions, meetings, procedures, services, unavailability, and other (illustrated in box 130). Those of ordinary skill in the art will appreciate that the list of event capabilities is not exhaustive and should not be interpreted as a limitation on the scope of possible event capabilities 125. Furthermore, the event capabilities 125 may be used to determine the specific event roles 120. As explained above with respect to specific participating objects 100, the event roles 120 define the way a participating object 100 contributes to a specific event. For example, the role of a participating object 100 that is a surgeon may be to perform the surgery, while the event role 120 of a hip replacement material asset may be to perform the role of being used by the surgeon during the medical procedure.

In addition to defining event capabilities 125 and event roles 120 for a particular participating object 100, financial profiles 135 are also generated. Financial profiles define the revenue and/or expense characteristics of a participating object as defined by event capability 125 and event role 120. Each participating object 100 in a medical procedure will have revenue generating or expense characteristic associated thereto. For example, a participating object 100 that is a surgeon generates revenue during a medical procedure, while a material asset that is used during the procedure may generate revenue or it may be an expense. Depending on the event role 120 the financial profile 135 for a particular participating object 100 may vary. For example, in certain event roles 120 a participating object 100 may generate revenue, while in other event roles 120 the same participating object 100 may result in an expense. In still other situations, a participating object 100 may generate revenue and result in an expense in the same event role 120. The financial profiles 135 may be used when coordinating medical procedures to maximize profit for the procedure, while not generating additional work tasks that result in further expense. Thus, by associating a financial profile 135 for a participating object 100 profitability can be increased without further convoluting the scheduling process.

In order to manage medical data in a more efficient and more profitable manner, the medical data may be defined as explained in detail below. In the formation of a medical management system a user may define at least one participating object 100. The participating object 100 may be selected to include, for example, an organization or entity, a person or resource, a material asset, and an informational asset. In a particular medical management system, the system is likely to have tens, hundreds, or even thousands of participating objects 100. For example, a certain medical clinic may be a participating object 100 at which numerous physicians, physician assistants, nurses, technical advisors, representative, and support staff may work. Each of the individuals that work at the medical clinic may also be a participating object 100. Additionally, certain medical equipment, third party resources, medical supply companies and the like may also be participating objects 100. The medical clinic may also have relationships with hospitals, other medical clinics, fill-in physicians and support staff, each of which may also be a participating object 100. As such, those of ordinary skill in the art will appreciate that defining the participating objects 100 thereby allows other aspects of medical management to occur.

After defining at least one participating object 100, a user may define an operational relationship between the at least one participating object 100 and a second participating object. As explained above, in a medical management system there may be tens, hundreds, or even thousands of participating objects 100. For each participating object, the operational relationships 110 with the other participating objects 100 may be defined, thereby allowing a user to link the necessary participating objects 100 when generating information and/or scheduling medical procedures. Examples of defining operational relationships 110 may include, for example, associated a physician with a particular medical clinic. The physician may also be linked to particular nurses and material assets specific to the physician's specialization. The physician may also be linked to hospitals where the physician performs procedures, as well as to third party suppliers from which the physician obtains medical supplies and/or services.

Along with defining operational relationships 110 between the participating objects 100, a user may define an event capability 125 for the at least one participating object 100. As explained above, the event capabilities 125 for each particular participating object 100 may vary according to the type of particular object 100. In one example where the participating object is a physician, the physician may be above to provide an admission, a call, be a member of a clinic, provide a consultation or deposition, be present at a meeting, perform a procedure, and provide a service. The physician may also indicate unavailability for certain event roles 120, define specialized practice areas, or otherwise indicate other event capabilities 125 that are not specifically enumerated. For example, unavailability may serve as a go/no-go status indicator for a particular event scheduled at a predetermined date and/or time. Unavailability may be used to define the status of human resources and/or material assets. Thus, when a user sets up a medical procedure, the available event capabilities 125 for the physician may be known. In another example, the participating object may be a medical device. The medical device may not be capable of providing an admission, making a call, being available at a clinic, providing a consultation or deposition, or providing a service. However, the medical device may be available for a procedure and could be required at a meeting. Those of ordinary skill in the art will appreciate that each participating object 100 will have event capabilities 125 specific to the participating object 100.

The user may further define an event role 120 for the at least one participating object 100. The event role 120 allows the user to determine how the participating object will participate in a particular medical event or procedure. For example, a physician may provide services by performing a surgery, while a nurse assists the physician, a medical supply company provides medical supplies, the physician performs the surgery in a hospital, and requires imaging information from a third party provider. In this example, various participating objects 100 (i.e., physician, nurse, medical supply company, medical supplies, hospital, imaging information, third party provider) each performed a specific event role 120 that was selected by the user from the available event capabilities 125. By defining the event role 120 the user may map out all necessary participating objects 100 for a medical procedure and ensure they are available as required.

The user may further define a financial profile 135 for the at least one participating object 100. The financial profile may allow the user to determine whether the participating object generates revenue or creates an expense. As such, the user may use various participating objects 100 that are otherwise fungible in order to maximize profit or achieve a desired financial result. Financial profiles 135 may be built into participating objects 100 for a defined event role 120 or event 100. Thus, a user may adjust the financial profile 135 for particular events 100 or event roles 120, thereby allowing the most current information to be provided to multiple users of the system.

While managing medical data in such a system as described above, a user may generate particular events. Examples of events a user may generate include the provision of medical services through, for example, appointments, clinics, operations, etc. Users may also generate a supply order, schedule patients' follow-up visits, order third party information or assets, etc. When generating an event, the user of at least one participating object 100 then generates an event for the at least one selected participating object 100. In most instances, the user will select multiple participating objects 100 when generating an event. For example, in scheduling a surgery, a user may select a first participating object 100 in the form of a surgeon. The user may then select a second participating object 100 based on the operational relationships 110 of the surgeon. For example, the user may select a hospital that is related to the surgeon in which the surgery will be performed. The user may then determine the number of support staff, such as physician assistants and nurses that will also contribute to the surgery. The support staff may be operationally related 110 to either the hospital, the surgeon, or both. The user may further order the necessary medical supplies from a medical supply company, as well as include third party service provider that supply a particular off-site asset, such as medical imaging. In this one procedure, the user has identified and linked numerous participating objects (i.e., the physician, support staff, hospital, medical supplies, medical supply company, third party suppliers, and medical images) in the generation of a single event. After generating the event, the user may review the financial profiles 135 to determine whether appropriate revenue is generated by the event.

After the event is generated, data representative of the generated event may be delivered to the user or another user of the medical management system. For example, upon generation of the event, the user will know how each participating object 100 is linked to the event. Additionally, data representative of the event may be delivered to other users, such as participating objects 100 in the event in order to coordinate scheduling, financial information, etc. In one embodiment of the event described above, upon the generation of the event scheduling information may be sent to all necessary participating objects 100 in the event. As such, the surgeon, support staff, hospital, medical supply company, and third party service provider will all know their event role, the date of the event, etc.

After the event is generated communication between the participating objects 10 may occur in real-time, thereby allowing each participating object 100 to know if any changes occur. In such a situation, data may be updated and delivered to a user in real-time through various types of electronic media such as, for example, telephonic communication, short message service technology (i.e., text messaging), email, proprietary computer software, and any other type of communication technology capable of sending updates and/or generated reports for a user to receive and review.

In addition to displaying updates to a user in real-time, a user may be automatically informed to a change in an event. For example, if the user is a participating object 100, such as a surgeon, and if medical supplies required for a procedure will not be received in time, the surgeon, as well as other effected participating objects 100 in the procedure may be automatically notified. As such, either the procedure date may be changed or different medical supplies or a different medical supplier may be procured. By automating the exchange of information, a change in an event may be communicated more rapidly, thereby informing all necessary parties, reducing wasted time, and helping to provide more efficient administration of medical services.

Figure 2:
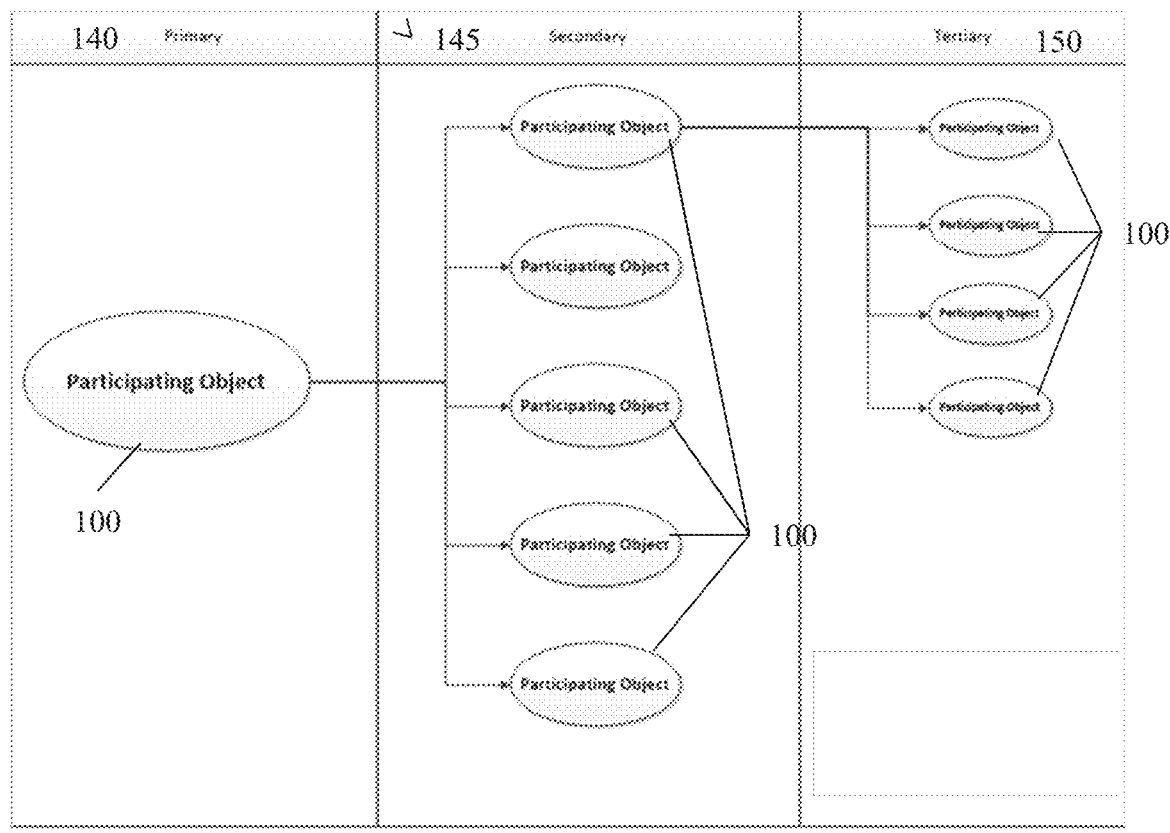
FIG. 2 is a block diagram of relationships between participating objects according to embodiments of the present invention.

Referring to FIG. 2, a block diagram of relationships between participating objects according to embodiments of the present invention is shown. Various types of participating objects 100 may be defined in medical management systems and processes according to embodiments of the present invention. As discussed above, participating objects 100 may generally include an organization or entity, a person or resources, a material asset, and an informational asset. In a particular medical management system or process, a participating object may be defined as a primary participating object 140. A primary participating object 140 may have relationships with other primary participating objects 140, or may have participating objects 100 that depend directly or indirectly on the primary participating objects 140. Participating objects 100 that depend on a primary participating object 140 are referred to herein as secondary participating objects 145. Secondary participating objects 145 may rely on information, data, financial accounting, allocation, etc. from one or more primary participating objects 140. In certain embodiments, in addition to secondary participating objects 145, tertiary participating objects 150 may also be included. Tertiary participating objects 150 are participating objects 100 that have a direct relationship with secondary participating objects 145, but may or may not have a direct relationship with a primary participating object 140. As illustrated in FIG. 2, the tertiary participating objects 150 have a direct relationship with one secondary participating object 145 and an indirect relationship with primary participating object 140. In other embodiments, tertiary participating objects 150 may have direct relationship with one or more secondary participating objects 145, and may have a direct or indirect relationship with primary participating object 140. Those of ordinary skill in the art will appreciate that multiple tiers of participating objects 100 may allow for data and/or informational control between working objects within a generated event or transaction.

For example, in a given scenario a primary participating object 140 may include a physician. The physician may have various secondary participating objects 145 such as, for example, nurses, assistants, medical supply companies, third party vendors, technical advisors, and the like. The secondary participating objects 145 may have a direct relationship with the primary participating object 140, thereby allowing an event change that effects either the primary participating object 140 or the secondary participating object to be communicated therebetween. The secondary participating objects 145 may also have direct relationships with tertiary participating objects 150. For example, expanding on the scenario identified above, medical supply companies, as a secondary participating object 145 may provide medical supplies, which are assets or tertiary participating objects 150. In another scenario, a third party vendor may be a secondary participating objects 145, which supplies medical images as a tertiary participating object 150.

In still other circumstances, tertiary participating objects 150 may be a person or entity. For example, primary participating object 140 may be a hospital, which employs various surgeons, physicians, etc., as secondary participating objects 145. Each physician may have staff that works exclusively for the physician in the form of a tertiary participating object 150. In such a situation, the tertiary participating objects may report directly to the secondary participating objects 145, e.g., a physician, while at the same time working for the primary participating object 140, e.g., the hospital. Thus, the tertiary participating objects 150 may have direct relationships with the secondary participating objects 145 and either direct or indirect relationships with the primary participating object 140.

In other embodiments, secondary participating objects 145 may be a secondary participating object to a primary participating object 140, but may also be linked to a second primary participating object 140 or may be a further subordinate to another participating object 100. In such a situation, the secondary participating object 145 may be a secondary participating object 145 to a primary participating object 140 while also being a tertiary participating object to a different secondary participating object. For example, a primary participating object 140 may be a hospital, having a secondary participating object 145 in the form of a physician. The physician may have a nurse that is a tertiary participating object 150 to the hospital. Thus in a certain medical service event or in a certain management practice the nurse may be a tertiary participating object 150. However, the nurse may also work for the physician at a private clinic not associated with the hospital. In such a situation, the physician may be the primary participating object 140 and the nurse may be a secondary participating object 145.

Those of ordinary skill in the art will appreciate that the primary, secondary, and/or tertiary relationships between participating objects 100 may be static within certain arrangements or may be dynamic, as different medical services are provided or events generated. For example, based on the specific generated events, a single participating object 100 may be a primary participating object 140 in a first event, a secondary participating object 145 in a second event, and a tertiary participating object 150 in a third event. In addition to the primary, secondary, and tertiary tiers discussed above, those of ordinary skill in the art will appreciate that in certain embodiments more tiers may be used. For example, in certain embodiments four, five, six, or more tiers may be used. In particularly complex organizational structures ten or more tiers may be used.

During use of tier-based participating object 100 structures during the medical management of data, for example, generating events, etc., at least one participating object 100 is defined as a primary participating object 140. In such a system, at least one second participating object 100 may be a secondary and/or a tertiary participating object 145/150.

To further explain the data structures of medical data management systems and process disclosed herein, several examples are set forth below. The examples provided are illustrative of how such managing medical data may be used in generating events, such as medical procedures. Those of ordinary skill in the art will appreciate that the examples provided below are not meant as a limitation on the scope of the present invention.

Figure 3:
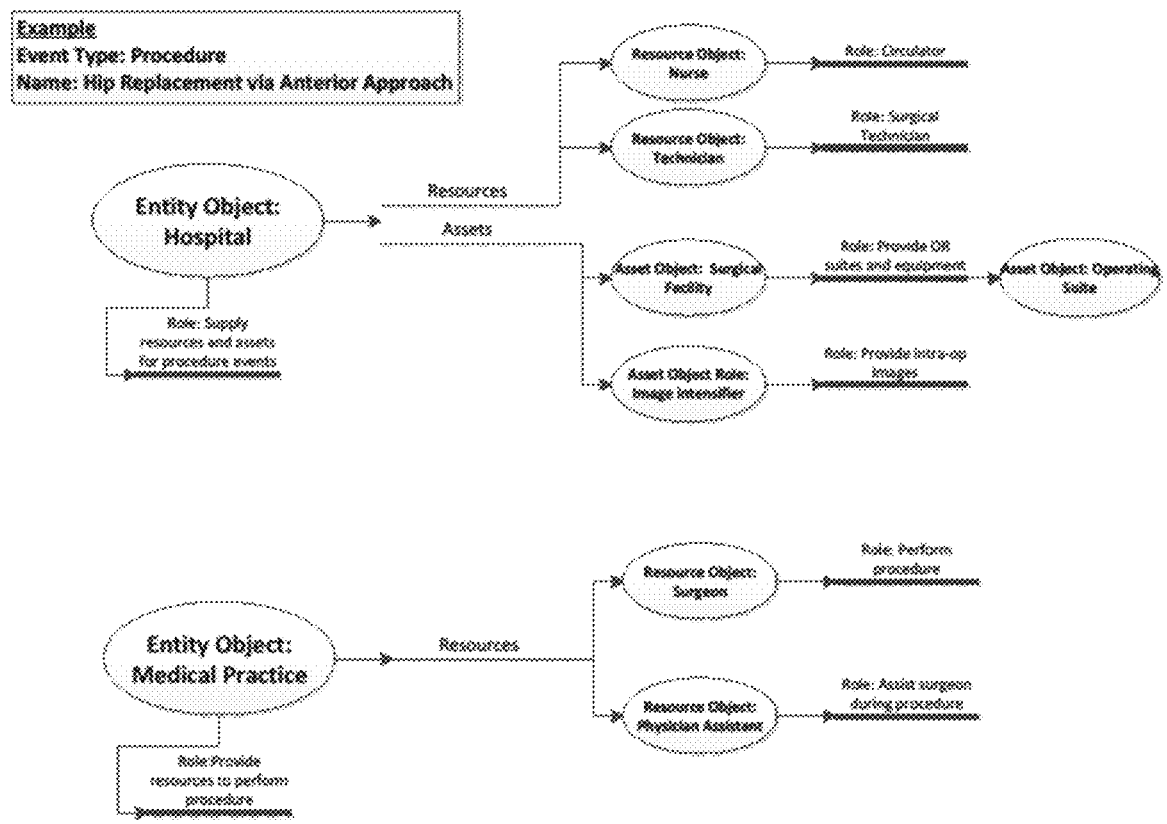
FIG. 3 is a flow chart diagram of an exemplary procedure according to embodiments of the present invention.
Figure 4:
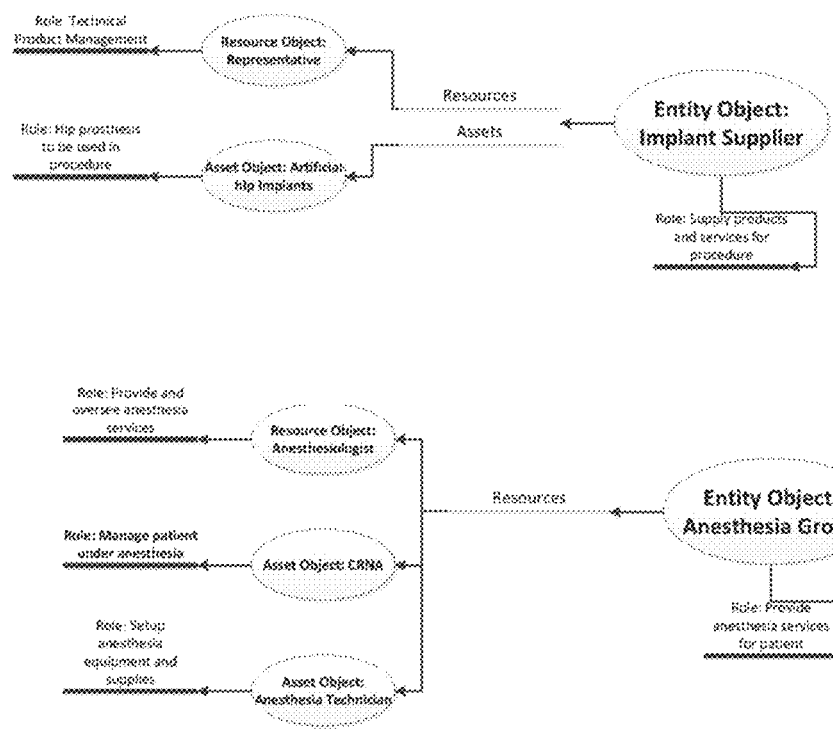
FIG. 4 is a flow chart diagram of an exemplary procedure according to embodiments of the present invention.

Referring to FIGS. 3 and 4 together, flow chart diagrams of an exemplary procedure according to embodiments of the present invention is shown. In this embodiment, the event type is a procedure for hip replacement via the anterior approach. All necessary participating objects have already been entered into the medical management system. The first participating object is an entity object defined as a hospital. The role of the hospital is defined to supply resources and assets for procedure events. There are several other participating objects that may be defined as primary or secondary participating events. For the purpose of this example whether the system uses tiered object structure does not impact the representation of the information for a user.

In addition to the hospital object entity, a resource object in the form of a nurse is provided. The role of the nurse is defined as a circulator. An additional resource object is also defined as a technician. The role of the technician is defined as a surgical technician. Both the nurse and the technician are classified as resources and provide help to the hospital during the procedure. In addition to resources, participating objects in the form of assets are also provided for the procedure. In this example, an asset object in the form of a surgical facility is provided with a defined role to provide operating room suits and equipment. An additional asset object in the form of an image intensifier is also provided with the role of providing intra-op images. In addition to the above identified asset objects, a third asset object is provided in the form of the operating suite that was recognized in the role of the surgical facility. Depending on the nature of the relationship between the surgical facility and the operating suite, independent participating object status for both may allow for a more efficient scheduling of the procedure. In certain embodiments, the operating suite may be defined as a secondary or tertiary participating object to the surgical facility or the hospital.

In addition to the components supplied directly or indirectly by the hospital, additional participating objects are also required for the procedure. In this embodiment a second entity object in the form of a medical practice is defined with the role of providing resources to perform the procedure. The resources to perform the procedure include a resources object in the form of a surgeon whose role is to perform the procedure and a resource object in the form of a physician assistant whose role is to assist the surgeon during the procedure. No assets are required by the medical practice, as the assets are provided in this example by the hospital.

With the hospital providing the location and staff, and the medical practice providing the surgeon and physician assistant, additional entity objects can be identified in the form of an implant supplier and an anesthesia group. The implant supplier is defined as having the role to supply products and services for the procedure. Resources for the implant supplier include a resource object in the form of a representative whose role is to provide technical product management. The asset provided by the implant supplier includes an asset object in the form of artificial hip implants. The role of the artificial hip implants is to be used as the hip prosthesis in the procedure.

In addition to the hospital, the medical practice, and the implant supplier, the anesthesia group is also defined as an entity object with the role to provide anesthesia services for the patient during the procedure. Resources provided by the anesthesia group include a resource object in the form of an anesthesiologist, an asset object in the form of a certified registered nurse anesthetist, and an asset object in the form of an anesthesia technician. The role of the anesthesiologist is to provide and oversee the anesthesia services. The role of the certified registered nurse anesthetist is to manage the patient under anesthesia, and the role of the anesthesia technician is to setup anesthesia equipment and supplies.

In the example provided above, all of the necessary services are provided by four participating entity objects, namely, the hospital, the medical practice, the implant supplier, and the anesthesia group. Each particular entity object has a defined role within the procedure. For example, the hospital provides the location and the staff, the medical practice provides the surgeon and the surgeon's assistance, the implant supplier provides the implants and a project management representative to oversee the transaction, and the anesthesia group provides an anesthesiologist, a nurse assistant, and a technician.

By defining the roles of each entity object required in the procedure, should changes be required that could modify the procedure, modifying or otherwise changing an aspect of the procedure is streamlined. For example, in the event the hospital is not able to supply the nurse or the facility, a substitute hospital or other participating object may be substituted to fulfill the role originally provided by the hospital. Similarly, if the implant supplier is not able to supply the implants by the required date, a substitute implant supplier may be selected or the date of the procedure rescheduled.

The compartmentalization of the entity objects also further defines expectations for what each component of the procedure is required to supply. By defining expectations before the procedure, each entity object can more effectively prepare and plan so that the procedure is successful. In the event there is a defect in one or more of the entity objects, the specific entity object with the defect can either correct the issue by substituting or modifying the resources or assets or can notify the other necessary entity objects so that a solution may be found.

Prior to the procedure, as explained above, a number of steps in the management of relevant medical data were taken. Initially the participating objects were defined. Initially, the required participating objects were the entity objects in the form of the hospital, the medical practice, the implant supplier, and the anesthesia group. Each of the entity objects had predefined relationships with resources and assets based on a defined operational relationship therebetween. Thus, an operational relationship was established between various participating entities, such as, for example, the hospital, the nurse, the technician, the surgical facility, and the image intensifier.

In order to determine which entity objects were required, as well as which resource and asset objects would be provided by the entity objects, event capabilities for the participating objects were previously defined. By defining the event capabilities, a user would know what dates certain participating objects were available, as well as the unique attributes of each participating object. For example, the user was able to schedule the hospital because event capability indicated that the hospital had the required surgical facility, the image intensifier, and the required staff. The user was also able to verify that the hospital and all necessary resources and assets were available for the desired date.

After verifying the event capabilities for the entity objects, the user could define the event roles for the entity objects, thereby allowing the entity objects and/or the necessary resources and assets to understand the defined role in the procedure. For example, the hospital provided certain nursing staff, however, the medical clinic and the anesthesiology group provided their own staff, respectively. Because the hospital knew in advance what resources and assets were being provided by the other entity objects, it did not have to incorrectly assign the incorrect staff for the procedure. Additionally, should an issue with a staff member becoming unavailable for the procedure, one of the other entity object may be able to provide the additional staff rather than changing the date of the procedure.

While not specifically discussed with respect to the example, each participating object also includes a defined financial profile. Because the financial profile is defined in advance, which scheduling the procedure each participating object, and specifically the entity objects, know the costs associated with the procedure. As such, each entity knows the costs and revenue associated with the procedure and can plan accordingly. The financial profiles can also assist a user in determining which staff to use in order to decrease medical costs associated with the procedure.

By compartmentalizing different resources and assets as particular participating objects for a procedure information may be transmitted between the different participating entities as required. For example, during the planning period before the procedure at least one event capability for a participating object may be modified. In one embodiment, the event capability may include an availability date of the hospital. Should the hospital become unavailable it is important that the data representative of the scheduling change be communicated to the necessary parties. In this example, the information would likely be distributed to all of the entity objects and at least the resource and asset objects that report to the hospital. As such, the resources and assets associated with the hospital can be reassigned to other tasks. Similarly, by notifying the medical practice, the surgeon and assistant may be reassigned. In certain embodiments, the change in scheduling data may be sent directly to resources and assets related to other entity objects. In this example, the surgeon and/or assistant may receive communication directly from the hospital.

When a modification to event capability occurs, it also provides a user the ability to more effectively reschedule or modify the parameters of a procedure in order to keep the procedure on track. In the situation where the hospital becomes unavailable, the user may find a different hospital, so that the procedure takes place on the same day at a different location. In other circumstances, the medical device supplier may be changed, a different anesthesiologist group may be used or a different medical practice may be substituted. Regardless of the event, the status of the procedure, as well as the status of the participating objects may be communicated to all or a selection of participating objects through direct communication. Direct communication may include, for example, use of electronic media that is accessible to the various participating objects. Specific examples include proprietary software programs that communicate and display real-time information to participating objects, as well as electronic communications through telephones, tablets, watches, computers, and all other electronic media communication devices as would be appreciated by those of skill in the art.

When a modification of an event capability for a participating object occurs, data representative of the modification may be delivered to one or more of the other participating objects. The data may comprise resource data, asset data, scheduling data, or any other type of data that is useful in administration of the procedure or other medical service.

Figure 5:
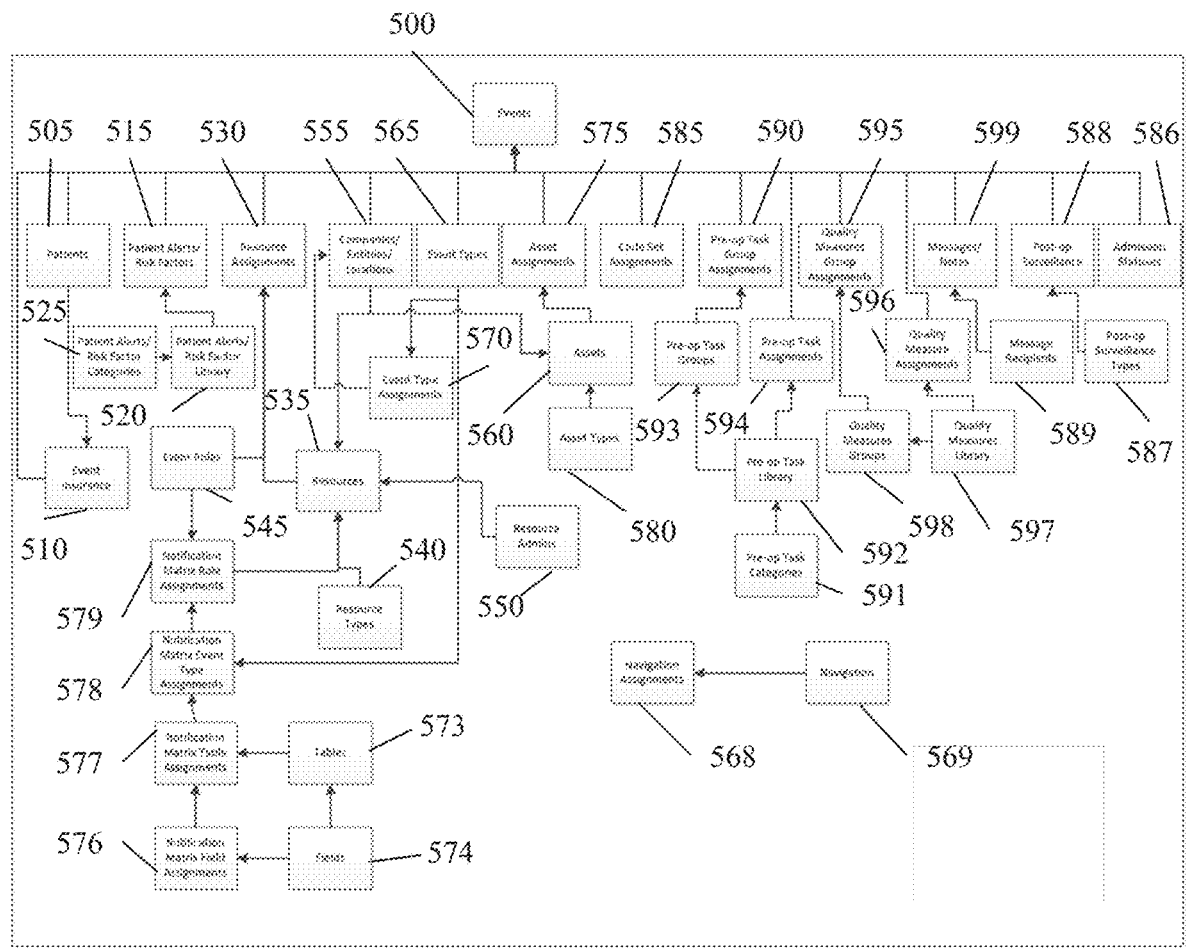
FIG. 5 is a flow chart diagram showing data structure according to embodiments of the present invention.

Referring to FIG. 5, a flow chart diagram showing data structure according to embodiments of the present invention is shown. The organization of data structure within embodiments of the present invention may further facilitate efficient scheduling and administration of medical procedures and services.

Embodiments of the present invention may be event 500 driven, thereby allowing information about patients 505 and participating objects to be communicated through the medical management system. Because the patients 505 and the participating objects are managed through the event 500 driven structure, a modification to the patient 505 or participating object may be administered through the same system. Thus, any modification to the event 500 may propagate throughout the medical management system to inform all participating objects of the modification. The event 500 driven system thereby removes inefficiencies present in conventional systems, saving time, and allowing for a more seamless approach to medical management.

While the event 500 is the top tier object various second tier objects allow for the administration of a particular medical event. The patient 505 is a second tier object, as the event 500 ultimately is generated as a result of the patient 505 requiring a service. The patient 505 also has insurance considerations. Accordingly, event insurance data 510 may be supplied, thereby providing the necessary participating objects in the event to know whether the patient 505 is covered, and if so, what type of coverage is applicable.

Certain aspects of the event 500 may also be dictated by patient alerts/risk factors 515. Patient alerts/risk factors may be supplied through information procured by the patient 505, or a participating object in the event 500. Examples of participating objects that may provide input include entities or resources, such as medical practice groups, hospitals, clinics physicians, and the like. Patient alerts/risk factors 515 may be selected from a patient alert/risk factor library 520, thereby allowing a user or participating object to note the alerts for other participants in the event 500 to view. For ease of entering the relevant data, and for ease of distribution of the data, patient alerts and risk factors may be categorized into patient alerts/risk factors categories 525. The categorical storage of potential alerts and risks may allow participants in the event 500 to have information about the patient 505 in a consistent manner that facilitates the event 500 as well as dissemination of the information.

The event is also subject to a second tier object that manages resource assignments 530. In each event, at least one resource will be assigned a role. The resource assignments may thus allow users of the medical manage system to know the assignments for each resource. Resource assignments 530 are ultimately providing the resources 535, subject to particular resource types 540 and event roles 545. Event roles 545 are predefined information that may be selected by particular resources when defining the roles that resources 535 may participate in. The resource type 540 may include a predefined list of the types of resources 535 available. For example, a user may know the type of event 500, and select a resource 535 of the correct resource type 540 and that is capable of fulfilling the required event role 545. In such a situation, a user may be scheduling a hip replacement surgery requiring a surgeon. The user may select a general category under resource type 540 for surgeon, then select a surgeon that specializes or is otherwise capable of performing a hip replacement based on event role 545 information. After selection, the resource 535 information along with the event role 545 information may be provided through resource assignments 530, thereby informing all participating objects in the event 500 as to the status of the resource 535. Information about resources 535 may be controlled through resource administration 550. Resource administration 550 may provide information about the resources or otherwise manage data related to various resources, should changes occur.

The events 500 may also include various participating objects in the form of companies, entities, and locations 555. The companies, entities, and locations 555 may provide information relevant to resources 535, as well as assets 560. For example, an entity 555, such as a hospital may provide resources 535 in the form of staff, as well as assets 560 in the form of operating rooms or other facilities. Thus, the companies, entities, and locations 555 may be directly involved in an event 500 or provide resources 535 required for the event 500.

As the medical management system disclosed in the present invention is event 500 driven, the event may be selected from predefined event types 565. The event types 565 may be selected by a user and may facilitate event type assignments 570, thereby allowing a user to access information about participating objects, such as companies, entities, and locations 555 that may have information about resources 535 and assets 560 that may be used in a particular event 500.

Similar to resource assignments 530, for a particular event 500 asset assignments 575 may also be defined. The asset assignments 575 may thus allow users of the medical manage system to know the assignments for each asset 560. Asset assignments 575 are ultimately provided assets 560, subject to particular asset types 580 and requirements of a resource 535. By providing centralized information with respect to asset assignments 575, a user may know what assets 560 are required for a particular event 500, as well as who is providing the asset 560.

Code set assignments 585 may also be defined, thereby allowing different participating objects as well as insurance and/or other payment types to receive accurate information about the procedures being performed in the event 500. Code set assignments 585 may be used to provide modifier codes along with long and short descriptions, as well as any applicable administrative, coverage, and/or pricing data. The codes may be used to represent items and supplies, as well as physician and non-physician services as may be required by Medicare, Medicaid, and private health insurers.

In addition to the actual procedure performed in the event 500, pre-op task group assignments 590 may also be defined. Pre-op task categories 591 may provide a list of categories for the types of pre-op activities that may be performed in preparation for an event 500. The pre-op categories 591 may be used to populate a pre-op task library 592 that is used in forming pre-op task groups 593. The pre-op groups 593 may then be used to define assignments for pre-op activities to be performed prior to the event 500. In addition to pre-op group assignments 590, specific pre-op task assignments 594 may also be defined. Pre-op assignments 594 may be defined by preselected pre-op task categories 591 as supplied by the pre-op task library 592. By having both pre-op task assignments 594, as well as pre-op group assignments 590, all pre-op tasks may be scheduled prior to the event 500, thereby facilitating efficient administration of pre-op activities.

Quality measures group assignments 595 along with quality measure assignments 596 may be used to define the quality of service supplied to the event 500. Quality measures group assignments 595 and quality measure assignments 596 may procure data from the quality measures library 597, which may be directly selected by a user when selecting quality measure assignments 596 or may go through quality measures groups 598 before being selected for quality measures group assignments 595.

In addition to information provided to participating objects, message and notes 599 may be entered into the system in order to inform parties participating in the event 500, including necessary participating objects, of other relevant information that may be useful in the event 500. The messages and notes 599 may receive data input from message recipients 589, as well as save data relevant to participating objects in the event 500.

After the event 500 occurs, there may be additional services that are monitored by the medical management system. In certain circumstances there may be post-op surveillance 588, which may be selected from predefined post-op surveillance types 587. Post-op surveillance 588 may be used to monitor patient 505 recovery, as well as provide follow-up services that may be required or recommended.

In addition to all activities surrounding the event 500, admission status 586 may also be monitored, thereby informing participants in the event 505 the status of the patient 505, as well as other information pertinent to the patient 505. Admission status 586 may also be used to monitor admission to a given facility. For example, the timing of admission may be tracked through admission status 586 in order to comply with federal, state, or private rules/regulations. In certain circumstances, organizations such as Medicare, Medicaid, or private insurance companies may have defined procedures that can be tracked and monitored using admission status 586.

In order to facilitate the administration of an event 500, various notifications may be used as part of the medical management system. Examples of notifications include notification matrix role assignments 579, notification matrix event type assignments 578, notification matrix table assignment 577, and notification matrix field assignments 576. The various notifications may be used to identify the tables and fields in the system that are added, modified, deleted, or otherwise experience a change. When a change occurs that requires notifying a user, administrator, or other participant in an event, the notifications may thereby define who is notified, when the notification is sent, how the notification is sent, etc. in certain embodiments, the notifications can be custom generated for each user, administrator, or participant in an event, thereby allowing only necessary parties to receive a notification. For example, in certain embodiments, particular participants may not require notification of a change, while other participants must be notified. The customization of notifications may thereby facilitate communication through the system, providing necessary information to users, administrators, and/or participants. A user or administrator may define various fields 574, which may include information about events 500, patients 505, event roles 545, resources 535, or other objects that are part of the medical management system.

The fields 574 may be supplied to the notification matrix field assignments 576. The notification matrix field assignments 576 may thereby communicate information about the fields to the notification matrix table assignments 577. By organizing the fields 574 into notification matrix field assignments 576 the fields 574 that are assigned to objects within the management system may be communicated to other objects within the management system. Thus, information about the specific fields 574 may be communicated to necessary objects, including, for example, patients 505, resources 535, and other participants in an event 500.

In certain embodiments, the fields 574 may be communicated and organized into specific tables 573. The tables 573 may include various combinations of field 574 data and/or other information or objects that are included in or are participants in the event 500. Tables 573 may thereby allow for the grouping or hierarchical organization of data, thereby allowing for more efficient communication of data within the management system.

In addition to receiving information from the notification matrix field assignments 576, notification matrix table assignments 577 may receive information/data from the tables 573. The notification matrix table assignments 577 may organize information about the event 500 supplied by the notification matrix field assignments 576 and the tables 573 so that the information/data may be supplied to participating objects or the event 500.

After data from the fields 574, tables 573, notification matrix field assignments 576, or other sources is supplied to notification matrix table assignments 577, the data may be supplied to notification matrix event type assignments 578. Notification matrix event type assignments 578 may further receive data about event types 565. Examples of data that may be supplied by the event types 565 include information about the specific event 500, such as, a type of procedure, appointment, surgery, or the like. The event type 565 data may then be combined with the field 574 and table 573 data provided by the notification matrix field assignments 576 and notification matrix table assignments 577 to define notifications about particular event type assignments. By organizing the fields 574 that may be required for a particular event type 565 into notification matrix event type assignments 578, the management system may be able to organize and track the requirements for a particular event type 565. The organization of the data may also provide for notifications about changes to requirements for an event type 565, thereby allowing participating objects in an event 500 to be notified of any changes that may be required for a particular event type 565.

Field 574 data and event type 565 data that is ultimately provided to the notification matrix event type assignments 578 may further be provided to notification matrix role assignments 579. Notification matrix role assignments 579 may also receive data from the event roles 545 and/or the resource types 540. Thus, the notification matrix role assignments may include data about specific resource types 540 that are available, as well as event roles 545 that may be required, along with event types 565 and fields 574, thereby allowing for role assignment to be generated. With generated role assignments, notification matrix role assignments 579 may communicate information to specific resources 535. Thus, a resource 535 may be provided information through notifications about a role in a specific event 500 or a role in an event type 565. Furthermore, should any aspect of a role, event type 565, or event 500 change, the resource 535 may be automatically notified.

Because data about event roles 545, event types 565, field assignments, table assignments, event type assignments, and other necessary data is combined in the notification matrix role assignments 579, a change to any aspect of the supplied data may populate throughout the management system. Notification matrix role assignments 579 may thereby provide updates to participating objects, such as resources 535 automatically or on an as needed basis, as required by the resources 535 or participating objects.

The medical management system may also include navigation data 569. Navigation data 569 may allow administrators or users of the system to interface with and/or communicate with participating objects in a particular event 500. In certain embodiments, navigation assignments 568 may be further specified, thereby directing administrators or users to specific information or data within the management system. Navigation data 569 and navigation assignments 568 may thereby direct administrators and users to specific data within the system as required by specific events 500 or changes to participating objects as part of the event 500.

Those of ordinary skill in the art will appreciate that the above defined organizational structure for the medical management system of the present invention is not inclusive of all tasks that may be performed before, during, or after an event 500. Rather, the structure defined above provides a hierarchical structure for the efficient distribution of information before, during, or after an event 500.

Figure 6:
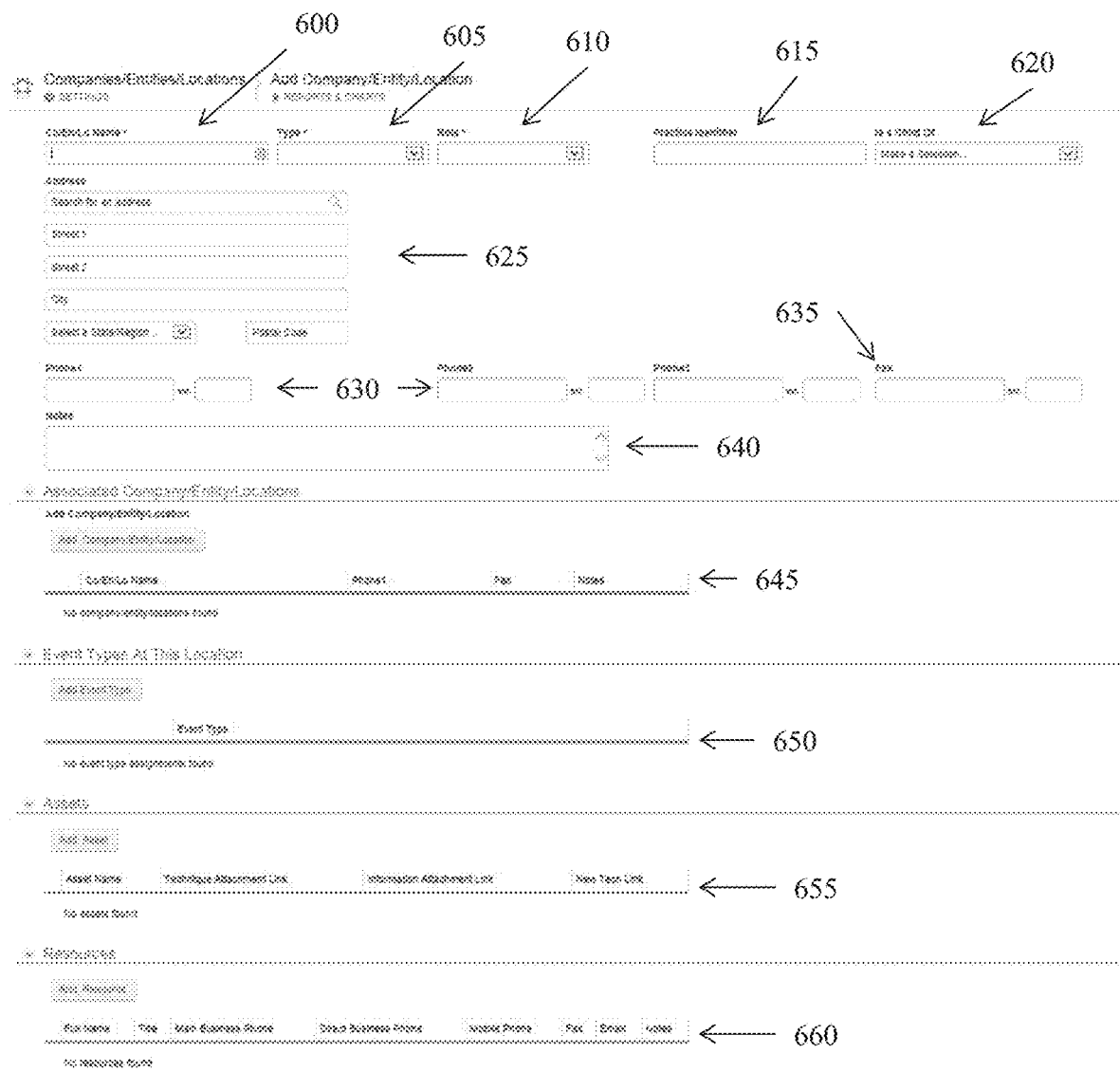
FIG. 6 is a data entry form according to embodiments of the present invention.

Referring to FIG. 6, a data entry form according to embodiments of the present invention is shown. When defining participating object information, a user may enter information specific to the particular participating object. For example, a user may define or otherwise provide an entity name 600. The entity name may include the name of a location, corporation, individual, or any other naming convention that allows the user to identify the participating entity. The user may further define the type of entity 605. Entity type 605 may refer to the qualitative properties of the entity. For example, an entity type 605 may include a hospital, clinic, medical practice, individual service provider, third party service provider, medical supply company, specialized practice group, or any other entity type that may provide goods and/or services during a medical procedure or in the provision of medical services.

The user may also define the role(s) 610 of the entity. The role(s) 610 of the entity may be used to determine whether a particular entity is appropriate for a particular procedure or medical service assignment. Additional fields that may be filled in by a user include a practice identifier 615 and a child selection 620. The practice identifier 615 allows the user to identify the practice types provided by the entity, while the child selection 620 allows the user to link the entity to other entities. To further identify the entity, address information 625, phone information 630, fax information 635, and notes 640 may be added to further define the entity.

In order to further facilitate medical service provision, the entity may also include associated entity information 645. The associated entity information 645 may be included in order to link entities that are associated with the participating object entity. The associated entities may be other participating object entities, assets, resources, or any other entity that may be associated with the participating object entity.

To assist identifying the types of events that may take place at a specific participating object entity, the user may define event types at the location 650. Defining the event types at a particular location allows a user to predefine all the different types of events a location can accommodate. This may be of particular importance when defining the types of events available at a physical location, such as a hospital or clinic.

A user may further define an entity by indicating they types of assets 655 and/or resources 660 available at the entity. Assets 655 may include, for example, types of technology, products, and/or services that are available. Resources 660 may refer to particular types of people, including nurses, physicians, representatives, technicians, information providers, etc., which may be used in the provision of medical services.

Figure 7:
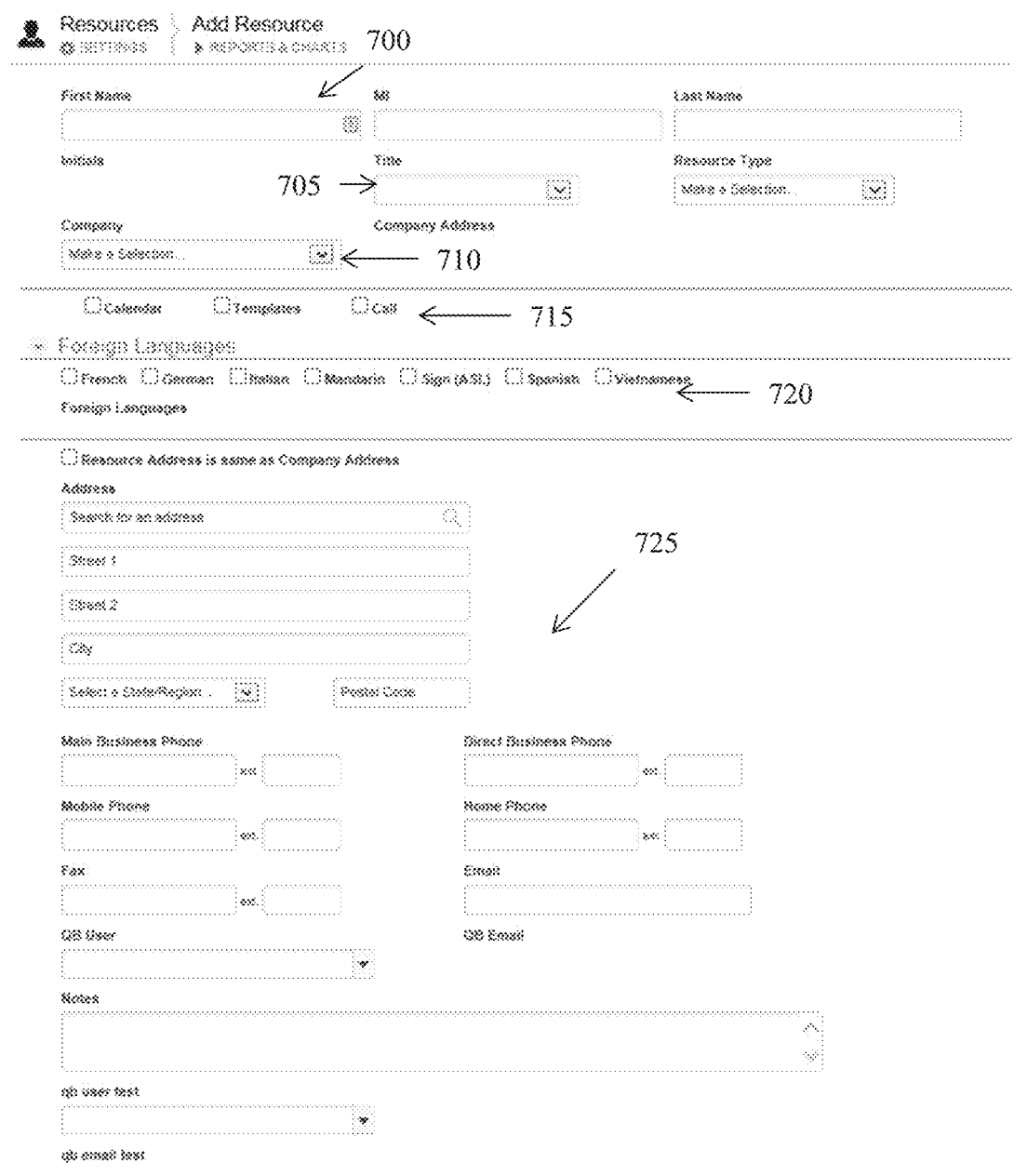
Figure 8:
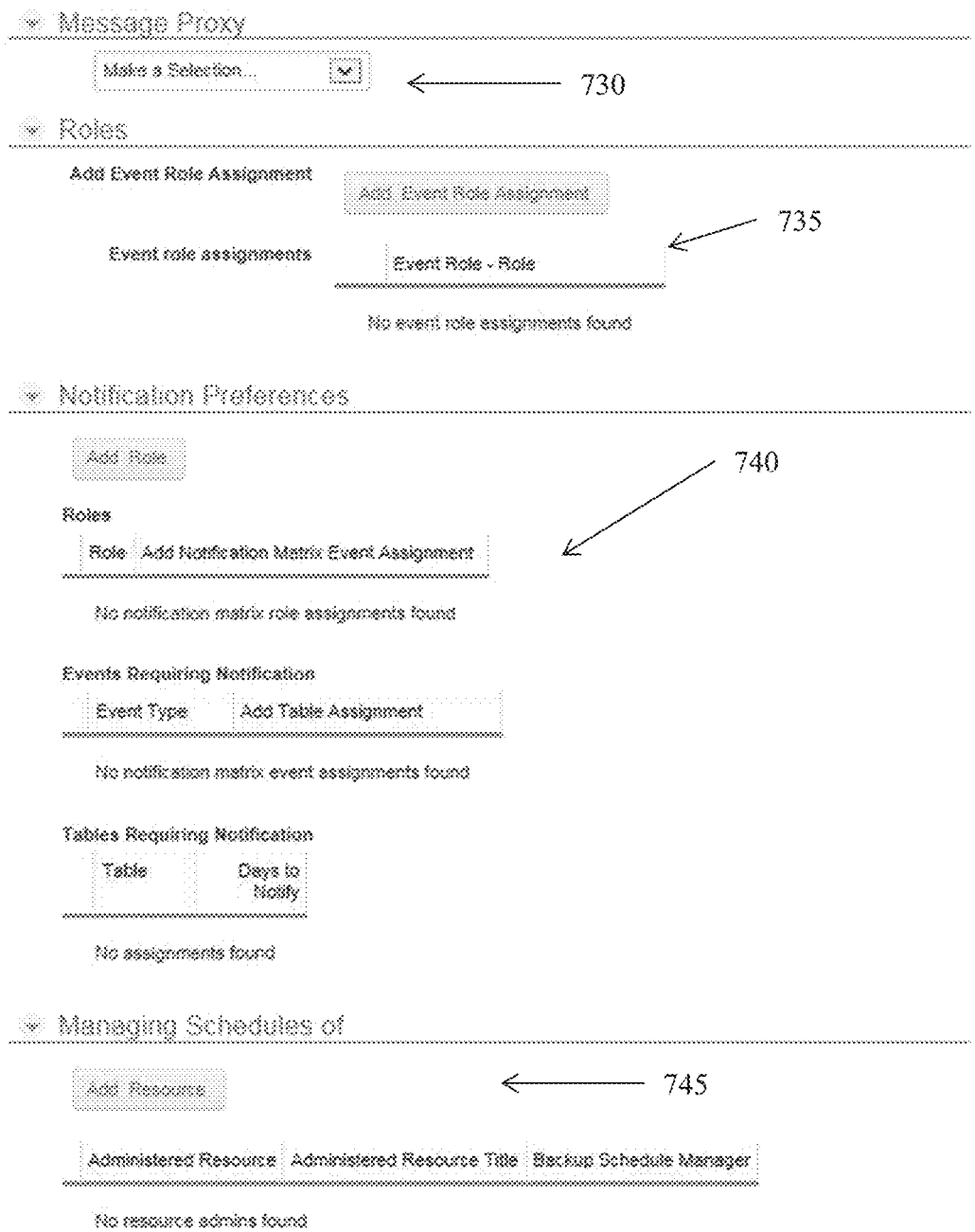
FIG. 8 is a data entry form according to embodiments of the present invention.

Referring to FIGS. 7 and 8 together, data entry forms according to embodiments of the present invention are shown. Resources are defined for particular participating objects, thereby allowing specific information regarding the resources to be known when an event is scheduled, generated, or modified. As a resource is generally an individual, a user may provide name information 700, title information 705, and company information 710 about the individual.

Additionally, the user may input information about the resource including calendar information, template information, and call information 715. This information may be used to allow user information about the resources calendar, templates that may be available, as well as allowing the user to be on call for a particular event. In certain embodiments, call information 715 may be used to designate a particular participant as on call for an entity, organization, patient, or other participating object. For example, a physician may be on call with respect to a patient, a hospital, an emergency room, a practice entity, or another participating objects. When a physician, or other participating object, is on call, the participating object may be required to be ready to respond to issues for a particular time period, e.g., for a full day, part of a day, for a weekend, for a week, or for a selected period of time, such as overnight from 10 pm to 8 am. In other circumstances, a type of participating object other than a physician, such as an organization may be on call. In such a situation, a hospital, emergency room, third party provider, or other participating object may be required to be ready to respond to the needs of another participating object. The resources may also be able to communicate in various languages. As such, the user may input information regarding the languages that the resource can communicate in by indicating foreign languages in foreign language section 720. In many instances, the resource is a member of a company or corporate entity. To provide information about the resources corporate membership, the user may include company information 725, including addresses, phone numbers, email, notes, and other information pertinent to the resources corporate affiliation.

The user may further define a message proxy 730 for the resource. The message proxy 730 may be used as a stand in for an otherwise unavailable resource. For example, if a resource, i.e., a person, is unavailable, message proxy 730 may receive messages for the resource until the resource becomes available again. Thus, a user may define who receives messages for the user if and/or when the user becomes unavailable. The user may further define different message proxies 730 for different contacts. In such a situation, a user, such as a physician, may have a first message proxy 730 for patients and a second message proxy 730 for third party providers. Because various message proxies 730 may be defined, the communication of information when a user is unavailable may be more efficiently facilitated. In order to define the roles of a resource, the user may also include role information 735. The role information 735 may be used in order to define a preselected or customized role for the resource in either all events or for selected roles in specialized events.

Notification preferences 740 may be entered by a user in order to define the type of notification required for a particular role. In certain circumstances a resource may not require notification, while in other circumstances a resource may request or require notification of a certain type for particular roles. Similarly, a user may define managing information 745, thereby allowing the schedule of a resource to be administered by a particular individual.

Figure 9:
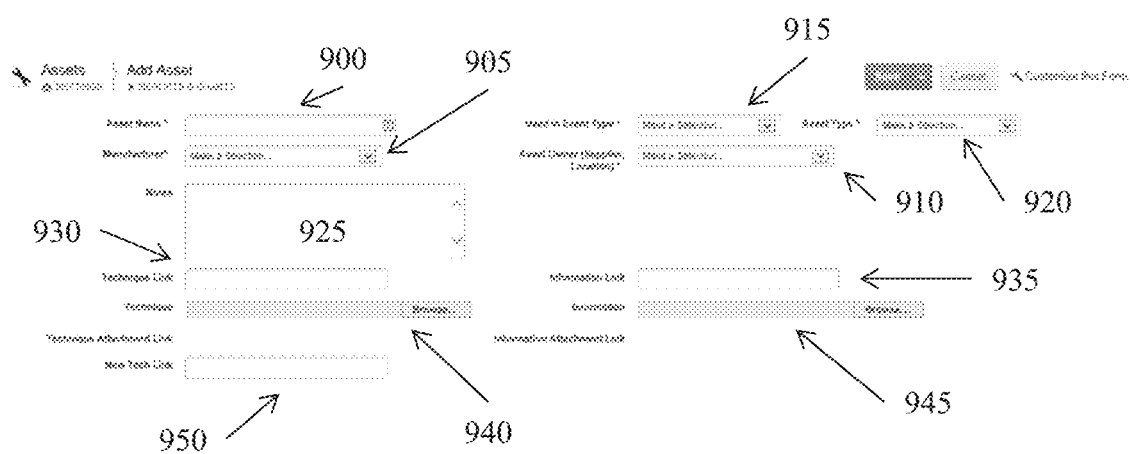
FIG. 9 is a data entry form according to embodiments of the present invention.

Referring to FIG. 9, a data entry form according to embodiments of the present invention is shown. Assets are defined for particular participating objects, thereby allowing specific information regarding the assets to be known when an event is scheduled, generated, or modified. In order to define an asset, an asset is given a particular name 900. The name may be the name of a corporate entity, a person, a supply, a device, a third party supplier, a location, a technology, etc. The asset name may also include a trade name or a nickname as determined by the user.

Many assets refer to products, devices, or services that are used by medical professionals. As such, the user may select or otherwise define a manufacturer 905. In addition to defining the manufacturer 905, a user may define or select an asset owner 910, such as a supplier or location of the asset. By allowing the user to enter, define, or selected the manufacturer 905 and the asset owner 910, the user can customize the asset to match an area, region, or other desired aspect for procuring the asset.

The user may also define the type of event 915 that the asset is used in. By selecting the type of event 915 that the asset is used in, the user can predefine the assets that may be required for a particular procedure or service, thereby streamlining the scheduling process. Additionally, the user may define an asset type 920, which may be selected from a group of similar assets.

In addition to standardized fields that are filled in by a user, the user may also enter in notes 925 particular to the asset. To further customize the asset information, the user may enter in a technique link 930, an information link 935, and upload technique data 940 and/or other information 945. By allowing technique data 940 and other information 945, information about the asset may be provided to a user without having to otherwise search for the information. Examples of technique data 940 and information 945 that may be uploaded includes information about how an asset is used in a procedure, product manuals, and the like. Finally, a new technology link 950 is provided whereby a user can include links to new assets that may be used with or in place of the existing asset. In addition to the specific examples identified above, those of ordinary skill in the art will appreciate that various other types of information may be linked to a particular asset including any information, documents, materials, and the like that may be germane to an event or specific to an asset.

Figure 10:
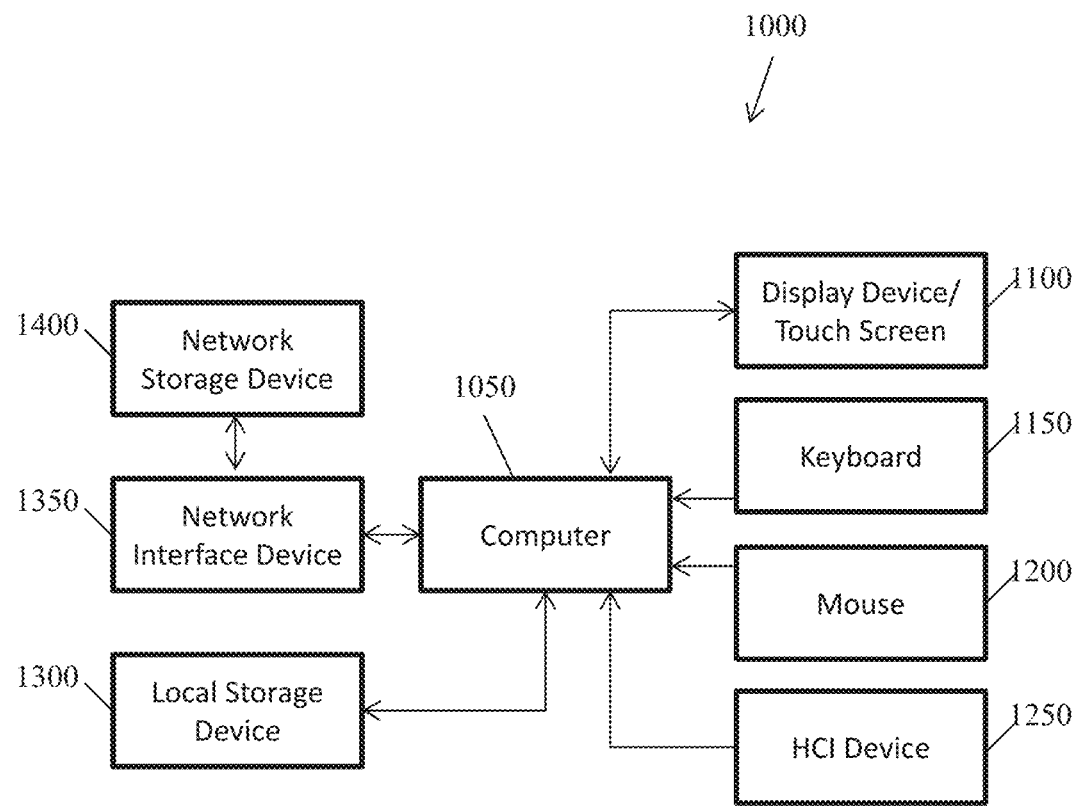
FIG. 10 is a schematic representation of a computer system according to embodiments of the present invention.

FIG. 10 shows a computing system 1000 in accordance with one or more embodiments of the present invention. Computing system 100 may include one or more computers 105 that each includes one or more printed circuit boards (not shown) or flex circuits (not shown) on which one or more processors (not shown) and system memory (not shown) may be disposed. Each of the one or more processors (not shown) may be a single-core processor (not shown) or a multi-core processor (not shown). Multi-core processors (not shown) typically include a plurality of processor cores (not shown) disposed on the same physical die or a plurality of processor cores (not shown) disposed on multiple die that are disposed in the same mechanical package. Computing system 1000 may include one or more input/output devices such as, for example, a display device 1100, keyboard 1150, mouse 1200, and/or any other human-computer interface device 1250. The one or more input/output devices may be integrated into computer 105. Display device 1100 may be a touch screen that includes a touch sensor (not shown) configured to sense touch. A touch screen enables a user to control various aspects of computing system 1000 by touch or gestures. For example, a user may interact directly with objects depicted on display device 1100 by touch or gestures that are sensed by the touch sensor and treated as input by computer 1050.

Computing system 1000 may include one or more local storage devices 1300. Local storage device 1300 may be a solid-state memory device, a solid-state memory device array, a hard disk drive, a hard disk drive array, or any other non-transitory computer readable medium. Local storage device 1300 may be integrated into computer 1050. Computing system 1000 may include one or more network interface devices 1400 that provide a network interface to computer 1050. The network interface may be Ethernet, Wi-Fi, Bluetooth, WiMAX, Fibre Channel, or any other network interface suitable to facilitate networked communications. Computing system 1000 may include one or more network-attached storage devices 1400 in addition to, or instead of, one or more local storage devices 1300. Network-attached storage device 1400 may be a solid-state memory device, a solid-state memory device array, a hard disk drive, a hard disk drive array, or any other non-transitory computer readable medium. Network-attached storage device 1500 may not be collocated with computer 1050 and may be accessible to computer 1050 via one or more network interfaces provided by one or more network interface devices 1350. One of ordinary skill in the art will recognize that computer 1050 may be a server, a workstation, a desktop, a laptop, a netbook, a tablet, a smartphone, a mobile device, and/or any other type of computing system in accordance with one or more embodiments of the present invention.

In certain embodiments, network interfaces, such as those described above, may be administered on cloud-based or on-demand computing systems. Cloud-based or on-demand computing systems are Internet-based systems that provide data to users and devices as required. Such systems rely on shared resources, thereby allowing networks, servers, storage devices, applications, and services to be accessed by multiple users at the same time. Administrators and/or users may access such cloud-based computing systems through desktop computers, laptops, tablets, phones, and/or any Ethernet enabled devices. By using cloud-based computing systems, data may be centrally stored and managed while allowing access to multiple users.

Computer systems according to embodiments of the present invention may include a processor, a system memory device, a network interface device, and a storage device. The storage device may include a non-transitory computer readable medium including software instruction that, when executed by the processor perform various operations.

For example, the various operations may include defining at least one participating object, defining an operational relationship between the at least one participating object and a second participating object. The operation may further include defining an event capability for the participating object, defining an event role for the at least one participating object, and defining a financial profile for the at least one participating object.

After the parameters are defined, the operation may include selecting at least one participating object, generating an even for the at least one selected participating object, and delivering data representative of the generated event to a user.

In certain embodiments, the at least one participating object may include an organization, a person, a material asset, and an informational asset. The event capability for the at least one participating object may include an admission, an on call status, a clinic, a consultation, a deposition, a meeting, a procedure, a service, and an unavailability. In certain embodiments, the financial profile for the at least one participating object may include one or more of a revenue and an expense.

Advantageously, embodiments of the present disclosure may provide automated systems and processes that reduce overhead expenses associated with labor intensive repetitive work tasks.

Advantageously, embodiments of the present disclosure may also provide automated systems and processes that communicate information necessary for practice operations.

Advantageously, embodiments of the present disclosure may also provide a cloud-based database for sharing information between service providers.

Advantageously, embodiments of the present disclosure may also provide a HIPAA compliant process for distributing information to service providers.

Advantageously, embodiments of the present disclosure may also provide a centralized information source for individuals, work related assets, schedules, and the like.

Advantageously, embodiments of the present disclosure may also provide information in a real-time environment via various communication tools such as, for example, phones, tablets, computers, and other portable and/or stationary electronic communication and/or processing devices.

Advantageously, embodiments of the present disclosure may also provide for scheduling for admissions, calls, clinics, consultations, depositions, meetings, procedures, services, unavailability, and other events that occur in the procurement of medical services.

Advantageously, embodiments of the present disclosure may also provide schedules and schedule events for individuals and/or groups.

Advantageously, embodiments of the present disclosure may also provide systems and processes that centralize the dissemination of information among medical employees, physicians, and other services providers without increasing the workload experienced by the service provider.

Advantageously, embodiments of the present disclosure may also provide for the elimination of routine work tasks such as, for example, schedule updating, reminder notifications, product updates, location updates, price updates, insurance modifications, as well as other tasks routinely performed by medical service providers.

Advantageously, embodiments of the present disclosure may also provide a template driven tool for the procurement of medical services.

Advantageously, embodiments of the present disclosure may also provide for the automated communication of scheduling information to hospitals, suppliers, and service providers.

Advantageously, embodiments of the present disclosure may also provide scheduling modification notification to people related to a particular event including, for example, physicians, clinical staff, hospitals, suppliers, and service providers.

Advantageously, embodiments of the present disclosure may also provide individually personalized notifications with respect to event timing and specific event triggers.

Advantageously, embodiments of the present disclosure may also provide documentation for procedure events including, for example, physician reports, medical clearances, laboratory results, test results, medical images, and medical image reports.

Advantageously, embodiments of the present disclosure may also provide for automated highlighting of specific patient medical risks and/or social risk factors.

Advantageously, embodiments of the present disclosure may also provide for checklists for schedulers to track requirements for complex medical events, such as procedures.

Advantageously, embodiments of the present disclosure may also provide automated alerts to clinical personnel with clinical related issues require attention.

Advantageously, embodiments of the present disclosure may also provide go/no-go indicators in the form of green-lights and red-lights that provide visual notification to system and process users. In addition to go/no-go notifications identified above, other visual notifications may be used to provide users updated information within the system.

Advantageously, embodiments of the present disclosure may also provide for the automated procurement of patient information and insurance information from a practice management system.

Advantageously, embodiments of the present disclosure may also receive and/or provide data/information to other systems, networks, databases through various types of connections including, for example, Ethernet, Bluetooth, WiMAX, Fibre Channel, cloud-based, or any other network interface suitable to facilitate networked communications Advantageously, embodiments of the present disclosure may also provide for the automatic reporting of billing codes and federal quality measures reports to clinician business offices or clearinghouse locations for processing at the end of clinical events.

Advantageously, embodiments of the present disclosure may also provide customized dashboards designed for specific job roles within the medical service fields.

Advantageously, embodiments of the present disclosure may also provide automated management dashboard displays to show past, present, and future practice metrics.

Advantageously, embodiments of the present disclosure may also provide dashboards that enable real-time clinic management including specific locations, times, and resources such as, for example, physicians, physician assistants, nurses, and medical assistants.

Advantageously, embodiments of the present disclosure may also provide real-time viewing and management of clinical resources and assets such as, for example, people, venues, equipment, instruments, and the like.

Advantageously, embodiments of the present disclosure may also provide an environment that allows third party vendors, such as imaging and billing companies, to integrate individual resources within a central practice management system.

While the present invention has been described with respect to the above-noted embodiments, those skilled in the art, having the benefit of this disclosure, will recognize that other embodiments may be devised that are within the scope of the invention as disclosed herein. Accordingly, the scope of the invention should be limited only by the appended claims.

What is claimed is:

1. A computer implemented method of managing and sharing, via a computer network, medical data, the method comprising:
    defining an event representative of a medical procedure as a top tier object within a data structure stored in memory accessible to one or more processors communicatively coupled to the computer network;
    defining at least one participating object, representative of a resource to be utilized during the medical procedure, in the data structure and associated to the event as a second tier object, the second tier object related, using a hierarchy within the data structure, to the top tier object;
    defining and maintaining, within the data structure, an operational relationship between the at least one participating object and a second participating object, the defining and maintaining performed by the one or more processors;
    defining an event capability for the at least one participating object, the event capability representative of an action to be performed by the at least one participating object for the medical procedure;
    defining an event role for the at least one participating object, the event role representative of a function to be provided by the at least one participating object for the medical procedure;
    defining a financial profile for the at least one participating object, the financial profile associated with the at least one participating object for the medical procedure;
    receiving, from a user interface device associated with a computer on the computer network, an indication of selection of the at least one participating object to perform the medical procedure;
    generating the event for the selected participating object, wherein generating the event includes utilizing the computer to propagate aspects of the event throughout the hierarchy within the data structure, the propagation of aspects of the event including updating interdependencies and functional relationships, as represented by associations between elements stored within the data structure, responsive to the generated event; and
    delivering data representative of the generated event to a user, the data representative of the generated event representing how each participating object represented within the hierarchy is affected by the generated event.

2. The method of claim 1, wherein the at least one participating object is selected from a group consisting of an organization, a person, material asset, and an informational asset.

3. The method of claim 1, wherein the event capability for the at least one participating object is selected from a group consisting of an admission, a call, a clinic, a consult, a deposition, a meeting, a procedure, a service, and an unavailability.

4. The method of claim 1, wherein the financial profile for the at least one participating object is selected from a group consisting of a revenue and an expense.

5. The method of claim 1, wherein the second participating object is a third party service provider.

6. The method of claim 1, further comprising displaying the data representative of the generated event to the user in real time.

7. The method of claim 1, wherein the data comprises resource information.

8. The method of claim 1, wherein the data comprises asset information.

9. The method of claim 1, further comprising informing automatically, via computer message transmission, the at least one participating object to a change in the event.

10. The method of claim 1, wherein the at least one participating object is a primary participating object.

11. The method of claim 1, wherein the at least one participating object is selected from a group consisting of a secondary participating object and a tertiary participating object.

12. The method of claim 10, wherein the second participating object is selected form a group consisting of a secondary participating object and a tertiary participating object.

13. A computer system to implement a method of managing and sharing, via a computer network, medical data, the computer system comprising:
 a processor;
 a system memory device communicatively coupled to the processor;
 a network interface device communicatively coupled to the processor; and
 a storage device accessible to the processor;
 wherein the storage device comprises a non-transitory computer readable medium comprising software instructions that, when executed by the processor, cause the processor to:
  define an event representative of a medical procedure as a top tier object within a data structure stored in the system memory device;
  define at least one participating object, representative of a resource to be utilized during the medical procedure, in the data structure and associated to the event as a second tier object, the second tier object related, using a hierarchy within the data structure, to the top tier object;
  define and maintain, within the data structure, an operational relationship between the at least one participating object and a second participating object, the defining and maintaining performed by the processor;
  define an event capability for the at least one participating object, the event capability representative of an action to be performed by the at least one participating object for the medical procedure;
  define an event role for the at least one participating object, the event role representative of a function to be provided by the at least one participating object for the medical procedure;
  define a financial profile for the at least one participating object, the financial profile associated with the at least one participating object for the medical procedure;
  receive, from a user interface device associated with a computer on the computer network, an indication of selection of the at least one participating object to perform the medical procedure;
  generate the event for the selected participating object, wherein generating the event includes utilizing the processor to propagate aspects of the event throughout the hierarchy within the data structure, the propagation of aspects of the event including updating interdependencies and functional relationships, as represented by associations between elements stored within the data structure, responsive to the generated event; and
  deliver data representative of the generated event to a user, the data representative of the generated event representing how each participating object represented within the hierarchy is affected by the generated event.

14. The computer system of claim 13, wherein the at least one participating object is selected from a group consisting of an organization, a person, material asset, and an informational asset.

15. The computer system of claim 13, wherein the event capability for the at least one participating object is selected from a group consisting of an admission, a call, a clinic, a consult, a deposition, a meeting, a procedure, a service, and an unavailability.

16. The computer system of claim 13, wherein the financial profile for the at least one participating object is selected from a group consisting of a revenue and an expense.

17. A computer implemented method of managing medical data, the method comprising:
 defining an event representative of a medical procedure as a top tier object within a data structure stored in memory accessible to one or more processors communicatively coupled to the computer network;
 defining at least one participating object, representative of a resource to be utilized during the medical procedure, in the data structure and associated to the event as a second tier object, the second tier object related, using a hierarchy within the data structure, to the top tier object;
 defining and maintaining, within the data structure, an operational relationship between the at least one participating object and a second participating object, the defining and maintaining performed by the one or more processors;
 defining an event capability for the at least one participating object, the event capability representative of an action to be performed by the at least one participating object for the medical procedure;
 defining an event role for the at least one participating object, the event role representative of a function to be provided by the at least one participating object for the medical procedure;
 defining a financial profile for the at least one participating object, the financial profile associated with the at least one participating object for the medical procedure;
 receiving, from a user interface device associated with a computer on the computer network, an indication of selection of the at least one participating object to perform the medical procedure;
 generating the event for the selected participating object, wherein generating the event includes utilizing the computer to propagate aspects of the event throughout the hierarchy within the data structure, the propagation of aspects of the event including updating interdependencies and functional relationships, as represented by associations between elements stored within the data structure, responsive to the generated event;
 identifying changes to data representative of a modification to at least one of the event capability for the at least one participating object and the event role for the at least one participating object; and
 delivering data representative of the modification to each participating object in the event, as indicated by the hierarchy within the data structure, to indicate how each participating object is affected by the generated event.

18. The method of claim 17, wherein the data representative of the modification comprises resource data.

19. The method of claim 17, wherein the data representative of the modification comprises asset data.

20. The method of claim 17, wherein the data representative of the modification comprises scheduling data.

\* \* \* \* \*